March 10, 1953 G. D. BUSH Plant Pat. 1,174
DWARF DOUBLE MOCK ORANGE PLANT
Filed July 14, 1951
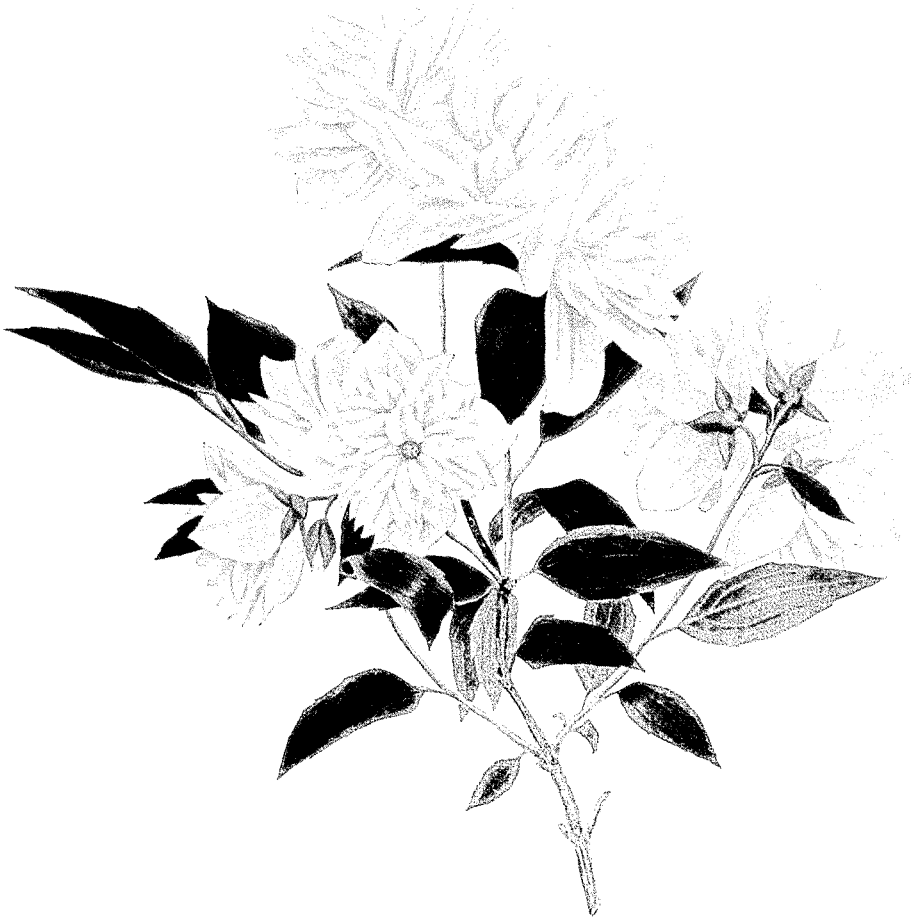
INVENTOR.
Guy D. Bush
BY
Williamson & Williamson
ATTORNEYS Patented Mar. 10, 1953

Plant Pat. 1,174

UNITED STATES PATENT OFFICE 1,174

DWARF DOUBLE MOCK ORANGE PLANT

Guy D. Bush, Minneapolis, Minn.

Application July 14, 1951, Serial No. 236,798

1 Claim. (Cl. 47—60)

My present invention relates to a new dwarf variety of flowering mock orange plant of the general botanical family known as Philadelphus.

The mother plant was developed by crossing the *virginalis* type with a double mock orange plant of the variety disclosed and described in my Plant Patent No. 538 granted August 11, 1942. The mother plant is located at my nursery in Minneapolis, Minnesota, and I have asexually reproduced young plants from the original mother plant at my nursery 3948—15th Avenue South, Minneapolis, Minnesota, by planting cuttings taken from the mother plant.

The accompanying original drawing shows a typical stem or cane with a plurality of typically positioned flower stems growing outwardly therefrom with the clusters of blossoms on the outer end portions thereof, and illustrates typical colors of all parts of my plant which are shown.

My new dwarf double mock orange embodies the characteristics of both the *virginalis* and the mock orange plant of my Plant Patent No. 538, hereinafter referred to merely as my patented variety. My new plant is distinguished from the *virginalis* and my patented variety in the following respects. The size of my new plant is considerably smaller than either of its parent plants. The blossoms, while being double as in my patented variety, are of smaller size and are clustered only at the ends of the blossom stems and each stem carries fewer blossoms. The general shape of the blossom petals around the outside of each blossom is generally similar to that of the blossoms of my patented variety. However, the inner petals are more densely clustered and the stamens of my new blossom are even more fully developed into completely formed petals than in the blossoms of my patented variety producing a substantially pure white center with practically no yellow coloring therein but clearly showing the pale green pistil at the center of the blossom. The leaves are smaller and more lanceolated than the leaves of my patented variety and are of similar general peripheral shape to the *lemoinei* with deeper serrations than my patented variety and more numerous serrations than *lemoinei* and having a darker green color than my patented variety but not quite as dark as *lemoinei*.

My new plant is characterized by its uniformly formed double flowers and its hardiness similar to my patented variety but is of considerably slower growth and produces a much smaller plant which is more readily adaptable for use in landscaping around a dwelling or other building. It is easily propagated and highly resistant to freezing or winter killing similarly to my patented variety. Neither the mother plant nor any of the young stock have up to the present time ever shown signs of injury due to the cold Minnesota climate.

The following is a detailed description of my new variety of double mock orange plant:

Shrub: Small, not as large as my patented variety or *virginal* is, somewhat smiliar to *lemoinei*. Vigorous; generally upright, canes more flexible near tops than my patented variety producing a more "weepy" plant, the branches of which are more divergent toward the tops than my patented variety. Short; vase formed; moderate growing speed; exceptionally hardy; very productive and easily propagated; regularly flowering; highly resistant to cold Minnesota winters.

Old canes: Slender; similar in color to my patented variety; bark lightly and regularly furrowed.

Lateral flowering branches or stems—after first year's growth: 2 to 5 inches long, average between 2 and 4 inches. More closely spaced along cane than my patented variety (about ½ to 1 inch apart). Slender and curving slightly upwardly from the drooping canes to position the face of all blossoms generally upwardly. Light green color, about the same as my patented variety.

New canes: Do not have flowers during first year's growth. Light green color, similar to my patented variety. Leaves are closely spaced and smaller than my patented variety but are larger than on old canes.

Leaves: 1 to 2 inches long, averaging about 1¼ inches long, shorter than my patented variety. ½ to 1 inch wide, averaging about ¾ of an inch, narrower than my patented variety. Color—darker green than my patented variety, not quite as dark as *lemoinei*—bottom surface whitish green. Slightly ovate acuminate but considerably more lanceolated than my patented variety, upper leaves more lanceolated than the lower leaves. Top surface smooth but veined, slightly rugose pubescent on back side. On new canes the lower leaves generally ovate gradually becoming generally lanceolated toward the top of the cane and curve downwardly generally similar to my patented variety giving the shrub a neat, uniformly colored appearance. Margin—more deeply serrated than my patented variety.

Peduncle: Short; slender; same color as the flower stems.

Flowers: Date of bloom in Minnesota about mid-June, depending upon weather conditions, about the same as my patented variety. Also blooms from tips of new growth later in the season, similar to *virginalis*. Largest blooms are about $1\frac{3}{16}$ inches across and the average size is about ⅞ inch across. Two to five blossoms clustered on outer end portion of blossom stem. Outer petals about the same shape as my patented variety; each bloom is double. Stamens have more fully developed into completely formed inner petals even than my patented variety with few if any undeveloped stamens, thus producing a pure white center with practically no yellow coloring but clearly showing the pale green pistil exactly at the center of the blossom. Anthers of undeveloped stamens (if any) are orange yellow similar to my patented variety with a white filament, pistils are light green. Pure white flower; sweet scented, similar to my patented variety.

Sepals of calyx: Star shape, generally four-pointed, but sometimes five and occasionally six. Ovary bulges outwardly generally similar to my patented variety. Buds generally similar to my patented variety.

The flowers above described and the plants producing the same will vary slightly in detail depending upon the climatic conditions under which they are grown. Propagated cuttings from the mother tree have produced flowers during their second year's growth similar to my patented variety.

What I claim is:

A mock orange plant substantially as herein shown and described characterized by the dwarfed size, the highly flexible canes, the small size and lanceolated shape of the leaves, the uniformly double blossoms, the closely clustered blossoms on the end portions of each flower stem, the sweet scent of its flowers, its vigor and hardiness, its ability to withstand extremely cold weather without winter killing, and its ease of propagation.

GUY D. BUSH.

No references cited.